(12) United States Patent
Shukla et al.

(10) Patent No.: US 8,124,727 B2
(45) Date of Patent: Feb. 28, 2012

(54) USE OF MODIFIED METAL OXIDES FOR ENRICHMENT OF PHOSPHOPEPTIDES

(76) Inventors: Ashok K. Shukla, Ellicott City, MD (US); Mukta M Shukla, Ellicott City, MD (US)

( * ) Notice: Subject to any disclaimer, the term of this patent is extended or adjusted under 35 U.S.C. 154(b) by 169 days.

(21) Appl. No.: 12/288,646

(22) Filed: Oct. 22, 2008

(65) Prior Publication Data

US 2009/0105450 A1    Apr. 23, 2009

Related U.S. Application Data

(60) Provisional application No. 60/999,724, filed on Oct. 22, 2007.

(51) Int. Cl.
*C07K 1/14* (2006.01)
*C07K 17/00* (2006.01)

(52) U.S. Cl. .................. 530/344; 530/412
(58) Field of Classification Search .............. None
See application file for complete search history.

(56) References Cited

U.S. PATENT DOCUMENTS

2006/0177855 A1*   8/2006   Utermohlen et al. ............ 435/6

OTHER PUBLICATIONS

Ruiz-Taylor et al. "Monolayers of derivatized poly(L-lysine)-grafted poly(ethylene glycol) on metal oxides as a class of biomolecular interfaces", PNAS, Jan. 2001, vol. 98, No. 3, pp. 852-857.*

* cited by examiner

*Primary Examiner* — Suzanne M Noakes

(57) ABSTRACT

Use of modified metal oxides for the purification and enrichment of negatively charged biomolecules such as peptides, proteins, DNA, RNA, Lipids, carbohydrates, glyco molecules. These metal oxides are modified in such a way that the density of the Lewis acid group is reduced due to modification.

3 Claims, 1 Drawing Sheet

USE OF MODIFIED METAL OXIDES FOR ENRICHMENT OF PHOSPHOPEPTIDES

This application (Applicants) claims the benefit of priority date Oct. 22, 2007 of provisional application No. 60/999,724.

FIELD OF THE INVENTION

Here, we describe the use of modified metal oxide particles or film for the purification of molecules containing Phospho-groups. Phospho-group containing molecules means molecules that contain one or more Phospho-groups and the Phospho-group is covalently bound to another atom. Metal oxides such as $TiO_2$, $ZrO_2$ and other metal oxides (such as Al, Zn, Ti, Zr, Hf, Ga, In and Tl) bind to the Phospho group as Lewis acid-base pair. In pure metal oxides, the Lewis acid base pair formation is so strong that sometimes it becomes difficult to isolate the desired molecule. Besides the Phospho-group containing molecules, other negatively charged groups (such as carboxyl, sulfate) also bind selectively with the metal oxides.

BACKGROUND OF THE INVENTION

Definitions; Here we try to briefly explain the definition of the terms used but this is not limited to its vast definition.

Particles: can be porous or non-porous and be of any shape and size.

Metal oxide: Oxides of individual metals or mixed metal oxides, which contain more than one metal. Metal oxides may contain other elements or functional groups.

Modification of metal oxides: means that the surface density or number of active centers, which binds negative charged molecules, are reduced by some chemical reactions or physical means such as coating, covering, non covalent interaction.

Biomolecules: The molecules of biological source can be further modified or fragmented. This is not limited to proteins, peptides, DNA, RNA, lipids, small molecules such as vitamins, carbohydrates, oligosaccharides, and combination of these molecules.

In recent years, the proteomics field is growing very rapidly to elucidate the structure of proteins. The post translation modifications (PTM) of proteins, by attaching the groups such as phosphate, sulfate, acetate, oxalate, carbohydrates, lipids, and many other functional groups, make these proteins to biological functional proteins. The study of these PTM's is very important for understanding and study of the biological functions of the biomolecules. One of the most important PTM is the attachment of phosphate group on the proteins. The position of the phosphate group can be achieved by fragmenting the proteins by using proteases. After fragmentation of proteins, the peptides are formed which can be analyzed by Mass spectrometer, directly or after separation on HPLC (High performance Liquid Chromatography. The enrichment of such modified peptides is very important, because sometime, these peptides concentration is too low and can not be identified if large amount of non specific or unmodified peptides are present. For further analysis of the small amounts of these PTM peptides, enrichment and purification steps are needed. In recent years, there are a no. of publications on the applications of metal oxides such as $TiO_2$ or $ZrO_2$ for the enrichment of the phosphopeptides. However, there is a drawback in using the pure metal oxides since sometimes the multi phosphate groups in the same peptides bind so strongly that they can not be eluted back. It is also possible that other negatively charged functional groups such as carboxyl and/or sulfate or any other negatively charged groups can interact with the metal oxide and create a binding stronger then the phosphate group itself.

To overcome the above problem, here we describe the use of modified metal oxides for selective binding of the phospho group containing molecules. For example, the phospho-peptides or proteins can be easily purified by using the $TiO_2$ or $ZrO_2$. However, the phospho-proteins or -peptides also contain besides the phospho group, other negatively charged groups such as carboxyl, sulfate etc. These negatively charged groups also bind with the metal oxides. The bound negatively charged molecules on the metal oxide can be eluted from the metal oxide particles by using high pH or changing the buffer or solution conditions. If more than one negative charge is present, the binding is stronger and it is difficult to elute the phospho molecule from the metal oxide particles. Here we show the use of the modified metal oxides in which case the modifications reduce the density of the Lewis acid centers of the metal oxide particles. This also allows the selective binding of the phospho group and other negatively charged molecules. The interaction between the negatively charged molecules is reduced due to a lower no. of active centers (the density of the Lewis acid groups) at metal oxide. Therefore, the binding occurs between the Lewis acid group on metal oxide and phospho group of the molecule. Other negatively charged molecules, which do not contain the phospho group may not bind under the same condition in which the phosphate group binds.

Furthermore, once the active center is reduced at the metal oxide, the multi phospho groups of the biomolecules will not bind at multiple Lewis acid centers at the metal oxide. This will enable the elution of the phospho molecule from the metal oxide under less drastic conditions. This will also further enable the purification of more selective phospho molecules from other negatively charged molecules.

The various features of novelty, which characterize the above invention, are pointed out with particularity in the claims annexed to and forming a part of this disclosure. For a better understanding of the invention, its advantages and objects, reference is made to the accompanying drawings and descriptive matter in which a preferred embodiment of the invention is illustrated.

DESCRIPTION OF THE PREFERRED EMBODIMENTS

Figure 1:
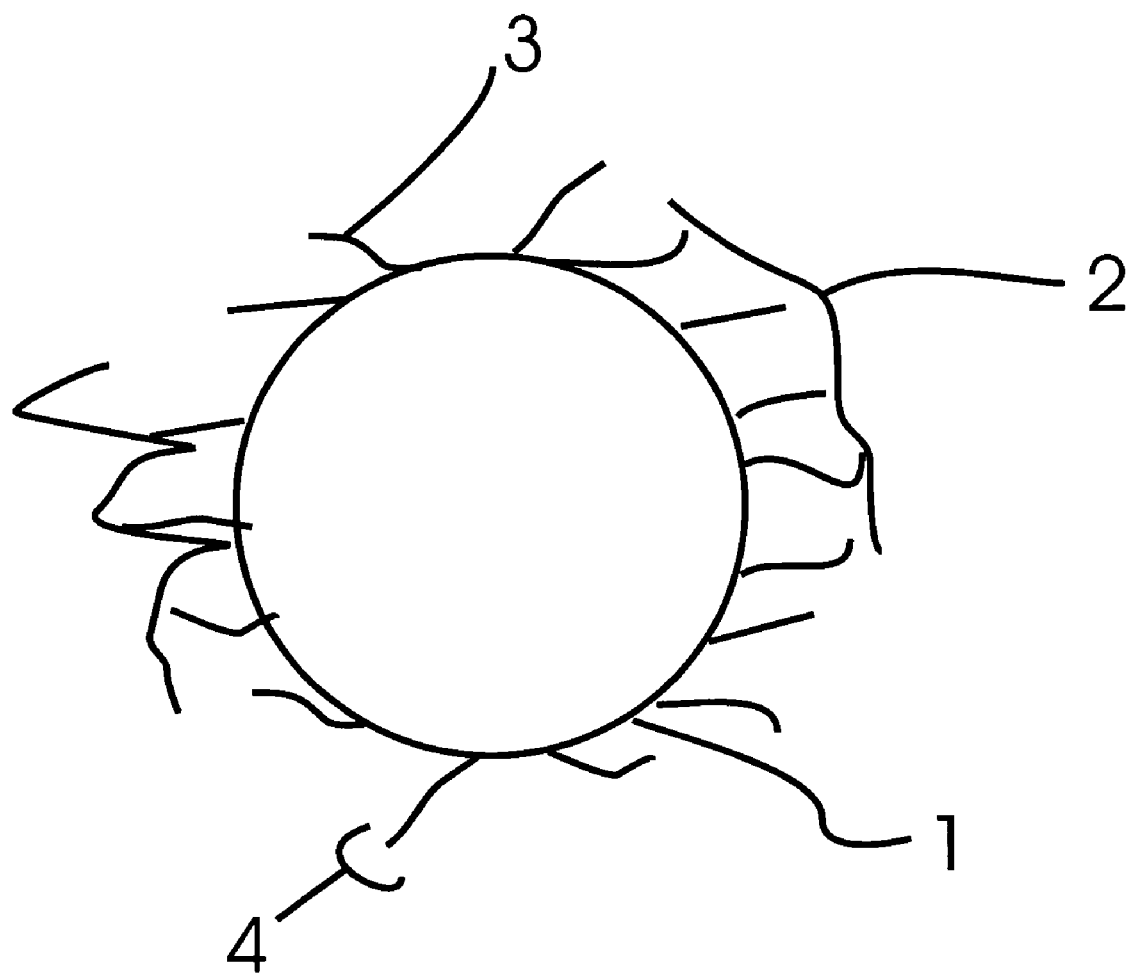
FIG. 1. is an expanded view of one embodiment of a metal oxide particle coated with non-covalently bound polymer.

FIG. 1 shows that the metal oxide particle (1) is coated with a polymer (2) and this polymer reduces the density of the Lewis acid group (3) at the surface of the particle. This reduction of the density may be random or symmetrical. The negatively charged molecule (4) can only bind to exposed Lewis acid group (3).

The modification on the metal oxide can be achieved by the chemical modification in such a way that it forms a stearic hindrance, by coating, covalently binding and polymerization of small molecules to form a net-like structure. Reduction of Lewis acid property is achieved by adding different metal oxides to form a mixed metal oxide or forming multi metal oxides or by any other chemical reaction or physical change or combination of both that can reduce the density of active Lewis acid center at the metal oxide. The number of Lewis acid groups can be reduced by coating the particles or layer by using the monomer and letting them polymerize at the surface of the particles or layer or film. This polymerization coating (2) can be either of negative or positive charge or of no charge, or a combination of two or all three.

The molecules containing the negatively charged groups contain the negative charge selected from the group comprised of phosphate, sulfate, carboxyl, any other negative charged functional group and combinations thereof. Modified metal oxides can be in the form of particles, film, coating or any other form, which can be used for the purification of molecules containing negatively charged groups. The shape of the said particle is either spherical, broken particles, porous, non porous, chromatographic particles of any shape and size (0.1-10,00000 micron). The said film is mono-layer or multi-layer on a surface and the said surface is porous, solid, and net or any other surface which can be coated with the said film. The thickness of the said film is from mono layer 10 mm thickness.

The said molecules containing negatively charged groups are bio-molecules such as proteins, peptides, lipids, carbohydrates, nucleic acids, DNA, RNA and are covalently bound to the negative group and these molecules have at least one or more negative charged groups. Furthermore, the said negative charged group is either terminal or between two functional groups in the same molecule. Single molecules may have more then one negative charge. Furthermore, same molecule may also have different types of negative charges as a result of attachment of different negatively charged groups, such as phosphate, sulfate, carboxyl or any other molecule which retains its negative charge after attaching to the biomolecules.

The modified metal oxides are Al, Zn, Ti, Zr, Hf, Ga, In and Tl or mixed metal oxides, or any other metal oxide, which can have Lewis acid character. Furthermore, the said modified metal oxide is a mixed metal oxide of Titanium, Zirconium, Hafnium, Aluminum, Gallium, Indium and other transition metal oxides or any metal oxide, which can have a Lewis acid character. The mixed metal oxide means a combination of two or more metal oxides.

The said modifications in metal oxides are created by means of chemical reaction, physical method such as coating, pressure, temperature; covalent binding or any other chemical or physical process or a combination of both, which reduces the number of Lewis acid centers at the metal oxide. Furthermore, modified metal oxide is coated on the particles such as silica, polymer, porous, nonporous silica or polymer particles.

These modified metal oxides can be used for the chromatography, sample prep, biochip, diagnostics or any other process or production of the biomolecules. Furthermore, modified metal oxides can be placed in columns for high performance liquid chromatography(HPLC), solid phase extraction column, single column, multiple column, 96, 384, 1536-well plates, film, embedded on the surface, for the purification of negatively charged molecules.

The said modified metal oxide coated plates can be used for MALDI mass spectrometer.

The modification can be performed during the purification step. A method for the purification and enrichment of the negative charged molecules can be developed by using the said modified metal oxide.

EXAMPLE 1

The random polyethylene (polymer) coated TiO2 (30 um) particles and non coated Tio2 particles are used. A peptide mixture obtained after the trypsin digestion of beta casein was used. Two mini columns of 50 ul containing TiO2 particle are used, one contains modified and other unmodified TiO2 particles. The binding of peptides is achieved at low pH (100 mM formic acid) and after several wash with water the peptides are eluted with 3% ammonium hydroxide. The samples of phosphopeptides are analyzed by HPLC and Mass spectrometer (MALDI). The difference in the binding of different phosphopeptides was observed.

While a specific embodiment of the invention has been shown and described in detail to illustrate the application of the principles of the invention, it is understood that the invention may be embodied otherwise without departing from such principles and that various modifications, alternate constructions, and equivalents will occur to those skilled in the area given the benefit of this disclosure and the embodiment described herein, as defined by the appended claims.

What is claimed is:

1. A method for purification of phospho-peptides/proteins from a mixture comprising:
   contacting said mixture with polyethylene coated porous titanium dioxide particles in a solution, wherein said polyethylene coating is random, at low pH to bind said phospho-peptides/proteins to said particles;
   washing extraneous peptides/proteins from said particles; and
   eluting and purifying said phospho-peptides/proteins at high pH.

2. The method for purification as in claim 1, wherein the size of the said particle is between 0.1-10,00000 micron.

3. The method for purification as in claim 1, wherein said Titanium dioxide is placed in a container selected from the group consisting of: column, tip, solid phase extraction column, multiple column, 96, 384, 1536-well plates, film, embedded on a surface, and combinations thereof.

* * * * *